United States Patent
Haras

(10) Patent No.: US 7,677,802 B2
(45) Date of Patent: Mar. 16, 2010

(54) METHOD AND PATIENT BED FOR POSITIONING A PATIENT IN A MEDICAL EXAMINATION SYSTEM

(75) Inventor: Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 324 days.

(21) Appl. No.: 11/779,989

(22) Filed: Jul. 19, 2007

(65) Prior Publication Data

US 2008/0016620 A1    Jan. 24, 2008

(30) Foreign Application Priority Data

Jul. 19, 2006    (DE) .................. 10 2006 033 500

(51) Int. Cl.
*A61B 6/04*    (2006.01)
(52) U.S. Cl. .................. 378/209; 378/20; 378/195
(58) Field of Classification Search .................. 378/20, 378/195, 205, 208, 209
See application file for complete search history.

(56) References Cited

U.S. PATENT DOCUMENTS

| | | | |
|---|---|---|---|
| 5,884,350 A | | 3/1999 | Kurze |
| 6,064,904 A | * | 5/2000 | Yanof et al. .................. 600/429 |
| 6,195,409 B1 | * | 2/2001 | Chang et al. .................. 378/20 |
| 2004/0081341 A1 | | 4/2004 | Cherek et al. |
| 2007/0038070 A1 | | 2/2007 | Tank |
| 2008/0013678 A1 | | 1/2008 | Mageri et al. |

* cited by examiner

*Primary Examiner*—Chih-Cheng G Kao
(74) *Attorney, Agent, or Firm*—Schiff Hardin LLP

(57) ABSTRACT

In a method for simplified positioning of a patient bed positioning information of a measurement position of the patient bed is recorded and retained as a forced stop position. The positioning of the patient bed between the measurement position ensues such that, given a movement of the patient bed from the withdrawn position, the positioning procedure is automatically halted upon reaching the measurement position.

17 Claims, 1 Drawing Sheet

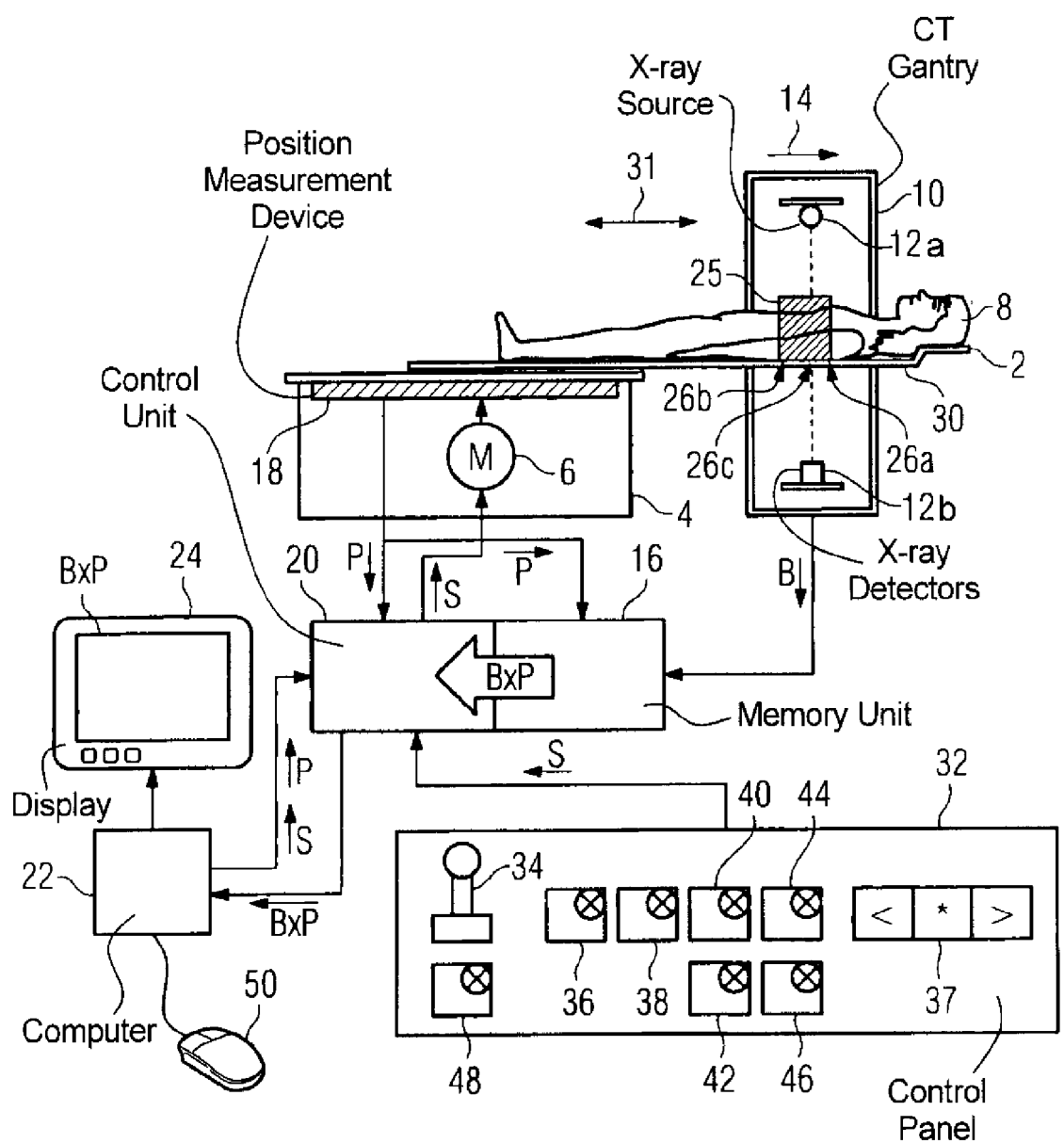

METHOD AND PATIENT BED FOR POSITIONING A PATIENT IN A MEDICAL EXAMINATION SYSTEM

BACKGROUND OF THE INVENTION

1. Field of the Invention

The present invention concerns a method for positioning a motorized positionable patient bed, as well as a patient positioning device for that purpose.

2. Description of the Prior Art

A motorized positionable patient bed is used for positioning a person in an examination with a medical imaging system. The position of the person to be examined is typically varied in steps such that data from a different body region of the person is acquired by the measurement device of the imaging system in the direction of the longitudinal axis of the body. Given each position change a measurement is implemented that is subsequently reassessed in a computerized manner in a diagnosis image. If a series of such diagnosis images (known as a scan) exists, the information of the individual diagnosis images can likewise be converted in a computerized manner into three-dimensional information. A very precise spatially-resolved diagnostic is possible in this manner. Such medical imaging systems are, for example, computed tomography systems and magnetic resonance tomography systems.

Computed tomography systems used are not only to generate diagnoses using the acquired image information, but also medical instruments (for example probes) in the human body can be exactly positioned with the aid of computed tomography. It is typical to initially generate an overview scan for prior planning of the medical intervention. The medical instrument to be positioned shown in a subsequently implemented scan in order to be able to monitor the position of the medical instrument as well as to be able to implement planning for the further procedure. For an optimally exact positioning of the medical instrument a multiple repetition of this procedure is often necessary.

A measurement (data acquisition) device of the imaging system often surrounds the person in a quite close radius such that a medical intervention for positioning a medical instrument can be implemented only in an uncomfortable manner or cannot be implemented at all. This confinement occurs due to the gantry that is used in computed tomography and the scanner bore in magnetic resonance tomography, which completely surround a body region of the examined person.

For a medical intervention, the person is therefore typically moved out of the measurement device of the imaging system by means of the patient bed sufficiently far that a treating physician can implement the medical intervention without spatial constriction. The movement of the patient bed occurs either by software control or by manipulation of control elements such as a joystick or a pushbutton. After a movement of the patient bed out of its measurement position and the implementation of the medical intervention, the patient bed is moved back into its measurement position again in order to be able to monitor the result of the manipulation by means of a scan.

The same body region of the person to be examined is thereby always measured by means of a scan. The scan is initiated by the treating physician with a further control element, most often a foot switch. In order to approach a measurement position with which data from this body region can be acquired by the measurement device, a treating physician typically notes the position of the patient bed (indicated by a numerical indicator) or learns this position from image information containing position information shown on a display element, and moves toward this position by manipulation of the control elements after implementation of the medical intervention. The resumption of this position, however, normally succeeds only after a repeated movement of the patient bed back and forth, in particular when the control element for the movement enables a number of advancement speeds for the positioning, and the advancement speed is successively increased given a longer triggering of the control element.

SUMMARY OF THE INVENTION

An object of the invention is to enable a simplified resumption of such a position.

The above object is achieved in accordance with the present invention by a method for positioning a patient bed relative to a medical examination system, and more specifically, relative to a data acquisition device of the medical examination system, wherein the patient bed, with a patient thereon, is moved to a measurement position in the data acquisition device, and this measurement position is recorded and stored as a forced stop position for the patient bed. The patient bed is then moved to a withdrawn position that is spaced from the measurement position. Subsequently, the patient bed with the patient thereon is again moved from the withdrawn position toward the measurement position and is automatically halted at the measurement position, using the stored forced stop position information, upon reaching the measurement position.

Positioning information of a measurement position of the patient bed thus is recorded and retained as a forced stop position. As used herein "measurement position" means a stripe-like region of the patient bed that can be acquired by the measurement device of the medical imaging system. The positioning of the patient bed ensues between the measurement position and a withdrawn position. As used herein "withdrawn position" means every position of the patient bed that does not correspond to the measurement position and is spatially different therefrom. "Spatial reference point" is the position that can be acquired by the measurement device. Given a movement of the patient bed from the withdrawn position, the positioning procedure is automatically halted given a reaching of the desired measurement position. A complicated movement of the patient bed back and forth in order, for example, to precisely adjust the measurement position using a visual indication, is no longer necessary. Rather, an arbitrary measurement position can be set with a single positioning procedure.

A treating physician thus is no longer reliant on the previously typically necessary assistance of an assistant in the movement of the patient bed in order to exactly occupy a measurement position. The treatment duration of the person to be examined is also shorter due to the time saving. Since a person should additionally move very little during such an intervention, the treatment comfort is improved to a significant degree.

In one variant, a defined scan position is established as a measurement position. The defined scan position is one of the positions of the patient bed that it adopts during the implementation of a scan. This can be, for example, the start or end position of the scan to be implemented. In particular, at the start position of the scan, after the medical intervention the patient bed is moved exactly into the position that serves as the start point for the implementation of a new scan. After the positioning of the patient bed the scan can thus be started immediately. The result of the medical intervention can be assessed very promptly in this manner.

In an embodiment the last scan position of the patient bed is established as a measurement position. If an implementation of a number of scans in succession is necessary for a reasonable evaluation of the medical intervention, this last scan position can be occupied in a simple manner after a new intervention.

In a further embodiment the position of the patient bed, correlated to a diagnosis image shown on a display element, is established as a measurement position. In other words: the assessing physician can precisely seek out that position that is particularly significant for him in the assessment of the scan by means of the display element and can occupy this position again upon a return of the patient bed after a medical intervention has occurred for the implementation of a new scan.

In a further embodiment the current real position of the patient bed is manually established as a desired position. Such a stored position thus can be reproducibly resumed again at any time.

In another embodiment a withdrawn position is established as a further forced stop position. Here it is an arbitrary position of the patient bed. By the establishment of a further forced stop position, the medical intervention can be particularly simply devised based on the spatial relationships, since a position that is particularly well accessible for the medical intervention can be occupied in a single positioning procedure.

By using one measurement position as a forced stop position and a withdrawn position as a further forced stop position, the patient bed can be moved exactly between these two positions. The patient bed thus stops both when its position is reached for the implementation of the medical intervention and when it has reached its measurement position from which the scan should be implemented. Not only the monitoring of the medical intervention by means of a scan but also the medical intervention itself can thus be implemented very quickly.

In another embodiment the patient bed automatically moves into its desired position and stops given a single actuation of a control element. A manual positioning by means of control elements is thus no longer necessary. A maximum operating comfort is achieved for the treating physician in this manner since the physician can, for example, actuate a special return movement button.

The illustrated possibilities for the establishment of a desired position as a forced stop position preferably are also combined with one another. For this purpose, corresponding control elements (such as buttons or the like) are provided with which a switching between the different desired positions is possible. These selecting control elements are appropriately executed with the logic of an OR-switch so that it is ensured that only one desired position is selected that is then occupies by the control element.

The above object also is achieved in accordance with the present invention by a position device for a patient bed that is operable to implement the method described above including all variations and embodiments.

In a preferred embodiment, a display element is provided for the display of the diagnosis images measured with the medical imaging system. During the measurement of the raw data from which the diagnosis images are later reconstructed, the positioning information of the patient bed is read out by means of the position measurement device. The raw measurement values are subsequently provided with this positioning information so that each diagnosis image also exhibits positioning information.

The patient positioning device appropriately has a number of indicator elements that are set up to indicate direction information for a movement of the patient bed by means of the control element to achieve a forced stop position and/or upon reaching this forced stop position. Additional information is given to an operator in this manner with regard to the direction the operator must move the patient bed in order to reach the intended measurement position. This can occur, for example, by illuminated indicators on which arrow symbols point in the movement direction in which to move. An indicator element can additionally be provided to the operator that indicates the reaching of the desired position. In this manner the operator receives an additional aid in addition to the halting of the patient bed in the desired position that indicates to the operator that this position has been reached.

In an embodiment, the patient positioning device has a sterile covering for the control element or control elements. This is, for example, a film that is disposed of after a single examination, or a reusable covering that, for example, is disinfected and/or sterilized after an examination. In this manner a sterile operation of the treating physician is also ensured given an intermittent actuation of the control elements.

In an embodiment the control unit is set up to slow the movement speed of the patient bed upon approaching a forced stop position. In this manner an abrupt braking of the patient bed is avoided. This is more gentle for the mechanism of the patient bed, and a smooth braking of the patient bed upon reaching the desired position is also considerably more pleasant for the examination subject.

The medical imaging system is advantageously a computed tomography system or a magnetic resonance tomography system or an angiographic computed tomography system.

BRIEF DESCRIPTION OF THE DRAWING

The single FIGURE schematically shows an embodiment of an inventive patient positioning device for a computed tomography system.

DESCRIPTION OF THE PREFERRED EMBODIMENTS

The central element of the patient positioning device is a patient bed 2 that is connected with a movement table 4 and is operated thereby. The positioning of the patient bed 2 occurs via a stepper motor 6 that is arranged in the movement table 4. A patient lying on the patient bed 2 is thus inserted in steps and in a defined manner into a gantry 10 (CT gantry 10) of a computed tomography system. An x-ray source 12a and x-ray detectors 12b arranged in the gantry 10 represent the measurement device of the computed tomography system.

For a measurement procedure, what is known as a CT scan, the patient 8 is inserted step-by-step into the gantry 10 in the feed direction 14 by means of the patient bed 2. At each step a measurement is implemented by the x-ray detectors 12 arranged in the gantry 10. The measured raw data are stored as image information B in a memory unit 16.

Furthermore, the current positioning information P of the patient bed 2 is recorded by a position measurement device 18 arranged essentially under the patient bed 2 in the entire range of the movement table 4. The image information B for a measurement position and stored in the memory unit 16 is provided with this positioning information P so that extended image information B×P results that includes the positioning information P.

This extended image information B×P is transferred from the memory unit 16 to a control unit 20 and from there to a workstation computer 22. The workstation computer 22 shows the extended image information B×P on a display 24 as a diagnosis image.

The control unit 20 additionally continuously records the current position of the patient bed 2 via the positioning information P generated by the position measurement device 18.

A medical intervention is implemented at a body region 25 of the person 8. First an overview scan of the body region 25 is generated for prior planning of the medical intervention. This body region 25 is subsequently subjected to a monitoring by means of a CT scan after every intervention. Every CT scan is initiated by means of a foot switch (not shown in the FIGURE). A positioning information P of a measurement position 26a, 26b, 26c is retained as a forced stop position by means of the control unit 20. The measurement positions 26a, 26b, 26c, are stripe-like regions of the patient bed, at each of which image data are directly acquired by the x-ray detectors 12.

The patient bed 2 is located in a withdrawn position 30 for the implementation of the medical intervention. The withdrawn position means any position of the patient bed 2 that does not correspond to the measurement position 26a, 26b, 26c and is displaced relative to this in the longitudinal direction 31 of the body.

The manual movement of the patient bed occurs by means of a control element arranged on a control panel 32 and executed with a joystick 34. A movement in the feed direction 14 ensues by means of the joystick 34 when the joystick 34 is moved in this feed direction 14. Analogous to this, a movement counter to the feed direction 14 ensues when the joystick 34 is moved counter to the feed direction 14. The movement of the joystick 34 is thereby translated into a signal S that is processed by the control unit 20 and is related to the step motor 6 as a prepared control signal. The stepper motor 6 thus translates the movement of the joystick 34 into a movement of the patient bed 2.

Upon reaching the measurement position established as a forced stop position, the positioning procedure is automatically stopped by means of the control unit 20.

In the exemplary embodiment various buttons 36, 38, 40, 42, 44, 46 and 48 with which the positioning of the patient bed 2 is significantly simplified are arranged on the control panel 32 in addition to the joystick 34. All buttons are illuminated in the activated state. This is symbolized in the drawing by a crossed-out circle arranged within the button which indicates the illumination device of the button.

The buttons 36, 38 and 40 enable the determination of different measurement positions 26a, 26b, 26c. They are linked in an OR-logic so that always only one button can be activated.

If the button 36 is activated, a defined scan position is defined as a desired position. If the medical intervention is effected on the person 8, a first CT scan for monitoring of the position of the introduced medical instrument is effected. For the CT scan the patient bed 2 is moved from a start position into an end position. The positioning information P (advantageously of the start position) is automatically stored after each CT scan in an internal memory of the control unit 20 as a measurement position 26a.

After an assessment of the image information B of the CT scan on the display element 24, the patient 8 is moved out from the gantry 10 counter to the feed direction 14 by means of the joystick 34. The medical intervention is subsequently implemented. If the patient bed 2 is now moved in the feed direction 14 by means of the joystick 34, the patient bed 2 automatically stops in the measurement position 26a defined as a forced stop position (the start position of the CT scan). The new CT scan for monitoring of the medical intervention just implemented can be implemented immediately without time loss.

Upon movement of the patient bed 2 by means of the joystick 34 the user receives direction information with regard to the movement direction of the joystick 34 via indicator elements 37 arranged on the control panel 32. If the patient bed is to be moved in the feed direction in order to occupy the start position of the CT scan, an indicator element illuminates that point in the feed direction. A corresponding indicator element that points counter to the feed direction 14 analogously illuminates when the patient bed 2 is to be moved counter to the feed direction 14. Reaching of the start position is signaled with a third indicator element. The user thereby receives the feedback that a further actuation of the joystick 34 is unnecessary and the positioning procedure is ended.

A second measurement position 26b can be provided, for example via an actuation of the button 38. In this case the positioning information P of the diagnosis image B×P directly displayed on the display element 24 is read out from the control unit 20 and established as a measurement position 26b (and therewith as a forced stop position). Given a change of the display on the display element 24, this measurement position 26b stored in the control unit 20 is updated in the control unit 20. This measurement position 26b corresponds to the position of the patient bed 2 with which the diagnosis image directly displayed on the display element was acquired. The movement to this forced stop position occurs by means of the joystick 34, precisely as in the manner already illustrated. The movement procedure automatically stops upon reaching the forced stop position. In this manner the treating physician can select under the various stored diagnosis images that diagnosis image that exhibits a particularly high information content for the physician. In this case an assumption of the measurement position 26b and a subsequent, immediate starting of a CT scan is also possible.

Finally, a measurement position 26c can be manually provided, for example via actuation of a further button 40. At the press of a button 43, that positioning information P of the patient bed that exhibits said positioning information P upon actuation of the button 42 is thereby stored in an internal memory of the control unit 20. Here as well a movement of the patient bed to this measurement position 26c (provided as a forced stop position) ensues by means of the joystick 34.

In a similar manner as described above, an activation of a button 44 enables the independent specification of a further withdrawn position 30 as a further forced stop position. If the button 44 is activated, the current position of the patient bed is stored by means of the actuation of a button 46. This position is also assumed by means of the joystick 34 and the patient bed 2 is automatically halted upon reaching this position. With the specification of a withdrawn position 30 as a further forced stop position, it is possible in a simple manner to bring the person 8 into a defined position by means of the patient bed 2 for the implementation of a medical intervention. After the implementation of the medical intervention, the patient bed 2 is moved (in the manner already described) into its measurement position 26a, 26b, 26c established as a forced stop position in order to be able to assess the result of the intervention by means of a CT scan to be acquired. By means of two forced stop positions it is therefore possible to implement a medical intervention in a quick manner and to assess the result of the medical intervention by means of a CT scan in a likewise quick manner.

The buttons 36, 38 and 40 are interconnected with one another according to an OR-logic so that always only one of the buttons 36, 38, 40 can be located in the activated state. In another embodiment, independent activation of the buttons 36, 38 and 40 is permitted and, for example, every approach or every achievement of a desired value is indicated with a separate indicator element comparable to the described indicator element 37.

All three different variants for a measurement position 26a, 26b, 26c are drawn in the FIGURE. In the FIGURE the patient bed is directly located in the measurement position 26c. Given an actuation of the button 42, this measurement position is stored. A complete CT scan of the body region 25 begins at the measurement position 26a. Given a movement of the patient bed in the feed direction 14, the body region 25 is successively measured. If a new CT scan is started from another position, this position is stored as a new measurement position 26a. The measurement position 25b corresponds with the image information B×P directly displayed on the display element 24.

The withdrawn position 30 lies longitudinal direction 31 of the body in the direction of the head of the person 8. If the patient bed is positioned by means of the joystick 34 after a selection of the button 44, the patient bed moves counter to the feed direction 14 and exposes the body region 25 at which the medical intervention is implemented.

An automatic movement of the patient bed back and forth is thus possible via an actuation of the control elements 34, 36, 38, 40, 42, 44, 46, 48 between the measurement positions 26a, 26b, 26c and the withdrawn position 30.

The button 48 induces the control unit 20 (by means of a control signal S) to move the patient bed into that forced stop position that is provided by means of one of the buttons 36, 38, 40 or 44. In this manner the treating physician no longer has to actuate the joystick 34 for the movement of the patient bed 2.

The control panel 32 is covered with a sterile covering for an examination of the person 8, which sterile covering is not shown in FIG. 1. The treating physician can thus implement both the medical intervention and the movement of the patient bed under sterile conditions.

The control unit 20 is set up such that the patient bed 2 is slowed upon an approach to a forced stop position so that a jerky braking of the patient bed does not occur upon reaching this forced stop position. The movement comfort for the person lying on the patient bed 2 is also increased in this manner.

The described forced stop positions can also be selected by the workstation computer 22 by means of a computer mouse 50. The control elements arranged on the control panel 32 are thereby simulated in software in a computer program. The corresponding control signals S as well as the extended image information B×P displayed on the display element 24 are passed to the control unit 20.

Although modifications and changes may be suggested by those skilled in the art, it is the intention of the inventor to embody within the patent warranted hereon all changes and modifications as reasonably and properly come within the scope of the inventor's contribution to the art.

I claim:

1. A method for positioning an automatically controlled patient bed relative to a data acquisition device of a medical examination system, comprising the steps of:
   by motorized movement, moving a patient bed to a measurement position in a data acquisition device of a medical examination system, and recording and storing information identifying said measurement position as a forced stop position of said patient bed;
   by further motorized movement of said patient bed, moving said patient bed from said measurement position to a withdrawn position that is spatially separated from said measurement position; and
   by further motorized movement of said patient bed, moving said patient bed from said withdrawn position back to said measurement position and stopping said motorized movement of said patient bed to halt said patient bed at said measurement position using said information stored as said forced stop position.

2. A method as claimed in claim 1 comprising setting said measurement position to be a defined scan position for said data acquisition device.

3. A method as claimed in claim 1 comprising, by said motorized movement of said patient bed, moving said patient bed through a plurality of scan positions in said data acquisition device, and setting said measurement position to be a last of said plurality of scan positions.

4. A method as claimed in claim 1 comprising displaying a diagnostic image of a patent at a display associated with said medical examination system, and, by said motorized movement of said patient bed, moving said patient bed to said measurement position dependent on said diagnostic image.

5. A method as claimed in claim 1 comprising, during said motorized movement of said patient bed through a plurality of positions in said data acquisition device, setting said measurement position to be a current, actual position of said patient bed in said data acquisition device.

6. A method as claimed in claim 1 comprising establishing said withdrawn position as a further forced stop position.

7. A method as claimed in claim 1 comprising controlling said motorized movement of said patient bed with a control unit having a manually actuatable control element, and automatically moving said patient bed to said measurement position under control of said control unit upon a one-time actuation of said control element.

8. A patient position device for positioning a patient in a data acquisition device of a medical examination system, said patient positioning device comprising:
   a motorized patient bed that is movable through a plurality of positions relative to said data acquisition device;
   a position measurement device that detects and stores at least one of said positions of said patient bed;
   a control unit that controls positioning of said patient bed dependent on manual operation of a control element of said control unit, said control element being operable to cause said control unit to move said patient bed to a measurement position in said data acquisition device, at which said position measurement device records information identifying said measurement position as a forced stop position;
   said control unit, dependent on further operation of said control element, causing said patient bed to move from said measurement position to a withdrawn position spaced from said measurement position; and
   said control unit, upon further operation of said control element, automatically causing said patient bed to move toward said measurement position and to stop at said measurement position using said information stored as said forced stop position.

9. A patient positioning device as claimed in claim 8 wherein said control unit establishes a defined scan position for said data acquisition device as said measurement position, said defined scan position being a position assumed by said patient bed during implementation of a temporally preceding data acquisition by said data acquisition device.

10. A patient positioning device as claimed in claim 9 wherein said patient bed is movable through a plurality of scan positions, and wherein said control unit establishes said measurement position as being a last of said plurality of scan positions.

11. A patient positioning device as claimed in claim 8 comprising a display at which diagnostic images obtained with said data acquisition system are visually shown, and wherein said control unit correlates said diagnostic images with respective position information of said patient bed detected by said position measurement device, and establishes one of said positions correlated with one of said diagnostic images as said measurement position.

12. A patient positioning device as claimed in claim 8 wherein said control unit establishes a current, actual position of said patient bed as a measurement position.

13. A patient positioning device as claimed in claim 8 wherein said control unit establishes said withdrawn position as a further forced stop position.

14. A patient positioning device as claimed in claim 8 wherein said control unit is programmed to automatically move said patient bed to said forced stop position upon a one-time actuation of said control element.

15. A patient positioning device as claimed in claim 8 comprising an indicator element that indicates directional information necessary for movement of said patient bed by operation of said control element to reach said forced stop position.

16. A patient positioning device as claimed in claim 8 comprising a sterile covering that covers said control element.

17. A patient positioning device as claimed in claim 8 wherein said control unit is programmed to slow a movement speed of said patient bed upon approaching said forced stop position.

* * * * *